United States Patent [19]
Kumazawa et al.

[11] Patent Number: 5,223,531
[45] Date of Patent: Jun. 29, 1993

[54] 1,3,2-DIOXATHIOLAN-S-OXIDE DERIVATIVES, METHOD FOR PREPARATION, AND USE THEREFOR

[75] Inventors: Satoru Kumazawa, Fukushima; Masanori Minoguchi, Tokyo, both of Japan

[73] Assignee: Kureha Chemical Industry Co., Ltd., Tokyo, Japan

[21] Appl. No.: 933,032

[22] Filed: Aug. 20, 1992

[30] Foreign Application Priority Data

Aug. 23, 1991 [JP] Japan ................................. 3-237488

[51] Int. Cl.$^5$ ...................... A61K 31/39; C07D 327/10
[52] U.S. Cl. ......................................... 514/439; 549/34
[58] Field of Search ............................ 549/34; 514/439

[56] References Cited

U.S. PATENT DOCUMENTS

| | | | |
|---|---|---|---|
| 3,395,226 | 7/1968 | Latham | 514/439 |
| 3,454,597 | 7/1969 | Tong et al. | 549/34 |
| 4,612,322 | 9/1986 | Ogata et al. | 514/383 |
| 4,863,505 | 9/1989 | Kumazawa et al. | 514/383 |
| 4,938,792 | 7/1990 | Kumazawa et al. | 514/383 |

FOREIGN PATENT DOCUMENTS 357404  3/1990  European Pat. Off. .

OTHER PUBLICATIONS

G. P. Blackburn et al., J. Chem. Soc., Series C, No. 2, pp. 257–259.

*Primary Examiner*—Glennon H. Hollrah
*Assistant Examiner*—Mark W. Russell
*Attorney, Agent, or Firm*—Burgess, Ryan & Wayne

[57] ABSTRACT

Disclosed is a 1,3,2-dioxathiolan-S-oxide derivative as represented by the general formula (I):

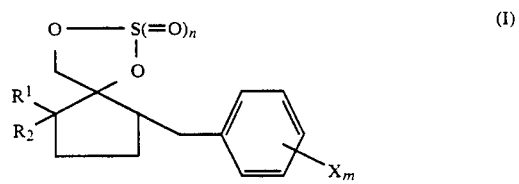

(where
$R_1$ and $R_2$ are identical to or different from each other and each is a hydrogen atom or a lower alkyl group;
X is a halogen atom, a cyano group, a lower alkyl group, a haloalkyl group or a phenyl group;
m is 0 or an integer from 1 to 5; and when small m is greater than 1 each x can be the same or different and n is 1 or 2).

A 1,3,2-dioxathiolan-2-oxide derivative of the compound as represented by the general formula (I-I) is prepared by reacting a hydroxymethylcyclopentanol derivative with thionyl chloride; and a 1,3,2-dioxathiolan-2,2-dioxide derivative (I-II) thereof is prepared by oxidizing the compound (I-I). The compounds (I) can be employed as fungicides and intermediate compounds for the preparation of azolylmethylcyclopentanol derivatives.

5 Claims, No Drawings

1,3,2-DIOXATHIOLAN-S-OXIDE DERIVATIVES, METHOD FOR PREPARATION, AND USE THEREFOR

BACKGROUND OF THE INVENTION

Field of the Invention

The present invention relates to novel 1,3,2-dioxathiolan-S-oxide derivatives a method for the preparation of the same, and a use for the same. The 1,3,2-dioxathiolan-S-oxide derivatives according to the present invention are useful as fungicides, and they can be employed as intermediate compounds for the preparation of an azolylmethylcyclopentanol known as an agricultural and horticultural fungicide or a plant growth regulator.

Description of the Related Art

U.S. Pat. Nos. 3,395,226 and 3,454,597 disclose that 1,3,2-dioxathiolan-2-oxide derivatives and 1,3,2-dioxathiolan-2,2-dioxide derivatives, among 1,3,2-dioxathiolan-S-oxide derivatives, are useful as fungicides.

Further, U.S. Pat. No. 4,612,322 (the Japanese counterpart being Japanese Patent Laid-open Publication (kokai) No. 25,990/1985 and the European counterpart being EP-A-133,248) discloses fungicidal 1,3,2-dioxathiolan-2-oxide derivatives.

It can be noted, however, that the 1,3,2-dioxathiolan-S-oxide derivatives disclosed in U.S. Pat. Nos. 3,395,226, 3,454,597, and 4,612,322 have no spiro structure.

SUMMARY OF THE INVENTION

As a result of extensive research and review of various compounds in which 1,3,2-dioxathiolan-S-oxides and a cyclopentane ring are joined through a spiro structure, it has been found that some compounds having the 1,3,2-dioxathiolan-S-oxides joined with the cyclopentane ring through the spiro structure are useful as fungicides and that they are useful as intermediate compounds for the preparation of azolylmethylcyclopentanol derivatives as will be represented by the general formulas (V) and (VI) below, which are disclosed in U.S. Pat. No. 4,863,505 (the Japanese counterpart being Japanese Patent Laid-open Publication (kokai) No. 149,667/1987 and the U.K. counterpart being GB-A-2,180,236) and U.S. Pat. No. 4,938,792 (the Japanese counterpart being Japanese Patent Laid-open Publication (kokai) No. 93,574/1989 and the European counterpart being EP-A-267,778). The present invention has been completed on the basis of this finding.

Therefore, the primary object of the present invention is to provide a 1,3,2-dioxathiolan-S-oxide derivative represented by the general formula (I) below:

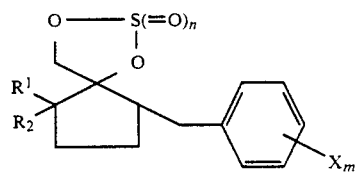

(where
$R_1$ and $R_2$ are identical to or different from each other and each is a hydrogen atom or a lower alkyl group;

$X$ is a halogen atom, a cyano group, a lower alkyl group, a haloalkyl group or a phenyl group;
$m$ is 0 or an integer from 1 to 5 and when $m$ is greater than 1 each $X$ can be the same or different; and $n$ is 1 or 2).

The present invention has another object to provide a method for the preparation of a novel 1,3,2-dioxathiolan-S-oxide derivative.

Another object of the present invention can be achieved by providing a method for the preparation of a 1,3,2-dioxathiolan-2-oxide derivative as will be represented by the general formula (I-I) below:

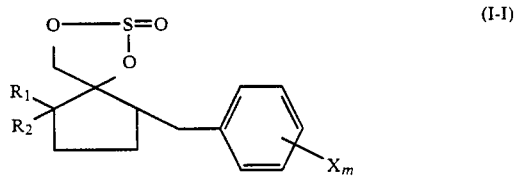

(where
$R_1$, $R_2$, $X$ and $m$ have the same meaning as in the general formula (I) above)
by reacting a hydroxymethylcyclopentanol derivative as will be represented by the general formula (II) below:

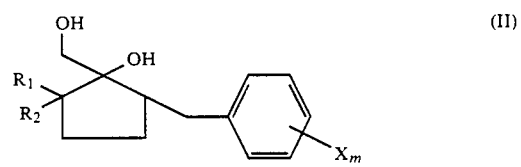

(where
$R_1$, $R_2$, $X$ and $m$ have the same meaning as in the general formula (I) above)
with thionyl chloride.

Further, another object of the present invention can be achieved by providing a method for the preparation of a 1,3,2-dioxathiolan-2,2-dioxide derivative as will be represented by the general formula (I-II) below:

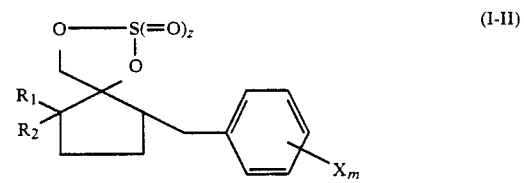

(where
$R_1$, $R_2$, $X$ and $m$ have the same meaning as in the general formula (I) above)
by oxidizing the sulfur atom of the 1,3,2-dioxathiolan-2-oxide derivative as represented by the general formula (I-I).

A further object of the present invention is to provide a method for the preparation of an azolylmethylcyclopentanol derivative from the 1,3,2-dioxathiolan2,2-dioxide derivative as represented by the general formula (I-II).

The further object of the present invention can be achieved by providing a method for the preparation of the azolylmethylcyclopentanol derivative as will be represented by the general formula (IV) below:

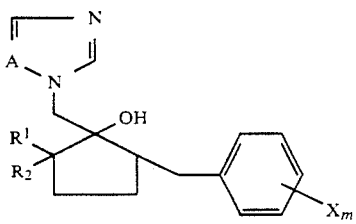

(where
R$_1$, R$_2$, X and m have the same meaning as in the general formula (I) above; and
A is a nitrogen atom and a CH group) by reacting the 1,3,2-dioxathiolan-2,2-dioxide derivative as represented by the general formula (I-II) above with an azole derivative as will be represented by the general formula (III) below:

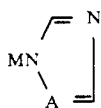 (III)

(where
M is an alkali metal atom or a hydrogen atom; and
A has the same meaning as in the general formula (IV) above).

The azolylmethylcyclopentanol derivatives as represented by the general formula (IV) are useful as horticultural fungicides and as plant growth regulators.

Therefore, a still further object of the present invention is to provide a fungicide containing the 1,3,2-dioxathiolan-S-oxide derivative as represented by the general formula (I) as an active ingredient.

Other objects, features and advantages of the present invention will become apparent in the course of the description of the preferred embodiments, which follows.

DESCRIPTION OF THE PREFERRED EMBODIMENTS

The 1,3,2-dioxathiolan-S-oxide derivatives according to the present invention may be represented by the general formula (I):

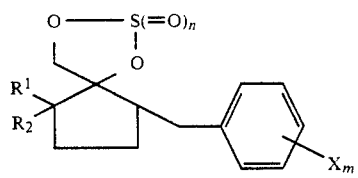

(where
R$_1$ and R$_2$ are identical to or different from each other and each is a hydrogen atom or a lower alkyl group;
X is a halogen atom, a cyano group, a lower alkyl group, a haloalkyl group or a phenyl group;
m is 0 or an integer from 1 to 5 and when m is greater than 1 each X can be the same or different; and n is 1 or 2).

The term "lower alkyl group" referred to in this specification is intended to mean a monovalent, straight-chained or branched, saturated hydrocarbon residue and it may include, for example, methyl, ethyl, propyl, iso-propyl, butyl, sec-butyl, tert-butyl and the like. The term "halogen atom" referred to in this specification is intended to mean, for example, chlorine atom, bromine atom, and the like. The term "haloalkyl group" referred to in this specification is intended to mean the lower alkyl group substituted by the halogen atom and it may include, for example, a fluorine-substituted lower alkyl group such as trifluoromethyl and the like.

The 1,3,2-dioxathiolan-S-oxide derivatives as represented by the general formula (I) include the following specific compounds as will be described in Table 1 below:

TABLE 1

| Compound Nos. | R$_1$ | R$_2$ | Xm | n |
|---|---|---|---|---|
| I-I-1 | CH$_3$ | CH$_3$ | 4-Cl | 1 |
| I-II-1 | CH$_3$ | CH$_3$ | 4-Cl | 2 |

Note:
The term "4-Cl" means a substitution of chlorine in the 4-position of the phenyl group.

The 1,3,2-dioxathiolan-S-oxide derivatives as represented by the general formula (I) may be prepared by the reaction scheme as will be shown hereinafter.

The following reaction scheme also represents the method for the preparation of the azolylmethylcyclopentanol derivatives by taking advantage of the 1,3,2-dioxathiolan-S-oxide derivatives as represented by the general formula (I) as intermediate compounds.

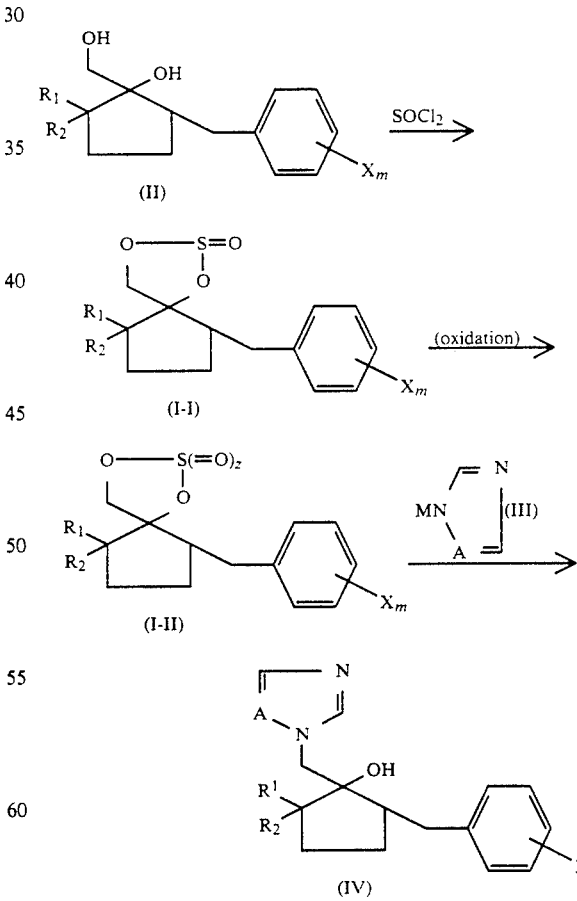

The 1,3,2-dioxathiolan-S-oxide derivatives as represented by the general formula (I-I) may be synthesized by reacting the hydroxymethylcyclopentanol derivatives as represented by the general formula (II) with thionyl chloride in an organic solvent in the presence of a base.

The organic solvent to be employed in the reaction as shown hereinabove may include, for example, a haloalkane such as dichloromethane, chloroform, dichloroethane, etc., an aromatic hydrocarbon such as toluene, etc., an aliphatic hydrocarbon such as hexane, heptane, isooctane, etc., and the like. The base to be employed may include, for example, an amine such as trimethylamine, triethylamine, N,N-dimethylaniline, N,N-diethylaniline, pyridine, and the like.

The reaction may be carried out at temperatures in the range of from approximately −40° C. to 100° C., preferably from approximately −10° C. to 30° C.

After the completion of the reaction, the 1,3,2-dioxathiolan-S-oxide derivatives as represented by the general formula (I-I) may be isolated from the reaction mixture by conventional separation methods such as column chromatography.

The 1,3,2-dioxathiolan-S-dioxide derivatives as represented by the general formula (I-II) may be prepared by oxidizing the sulfur atom of the 1,3,2-dioxathiolan-S-oxide derivatives as represented by the general formula (I-I) with an oxidizing agent in a solvent in the presence of a catalyst.

The oxidizing agent to be employed for the reaction as have been described hereinabove may include, for example, a halogen oxyacid salt such as a hypochlorite, a periodate, etc., and the like.

The catalyst to be employed for the reaction as have been described hereinabove may include, for example, a ruthenium derivative such as ruthenium oxide ($RuO_2$) or ruthenium chloride ($RuCl_3$).

The solvent to be employed therefor may include, for example, a polar solvent such as water, a lower alcohol, e.g. methanol, ethanol, etc., acetonitrile, N,N-dimethylformamide, and the like. These solvents may be employed singly or in combination of two or more. When the solvent is employed as a two-phase, water-organic solvent system, the organic solvent may include, for example, a haloalkane such as dichloromethane, carbon tetrachloride, etc., an ester such as methyl acetate, ethyl acetate, etc.

The reaction may be carried out at temperatures in the range of from approximately −40° C. to 20° C., preferably from approximately −10° C. to 10° C.

The 1,3,2-dioxathiolan-S-dioxide derivative as represented by the general formula (I-II) may be isolated from the reaction mixture by conventional separation methods.

It is to be noted that the 1,3,2-dioxathiolan-S-oxide derivative as represented by the general formula (I-I) contains isomers derived from its 2-oxide moiety. Accordingly, the compounds according to the present invention encompass those isomers within the scope of the invention.

The 1,3,2-dioxathiolan-S-dioxide derivative as represented by the general formula (I-II) can be utilized in a manner as will be described hereinafter. In other words, the 1,3,2-dioxathiolan-S-dioxide derivatives as represented by the general formula (I-II) can be reacted with the azole derivative as represented by the general formula (III) above in a solvent in the reaction scheme as have been shown hereinabove to give the azolylmethylcyclopentanol derivatives as will be represented by the general formulas (V) and (VI) below:

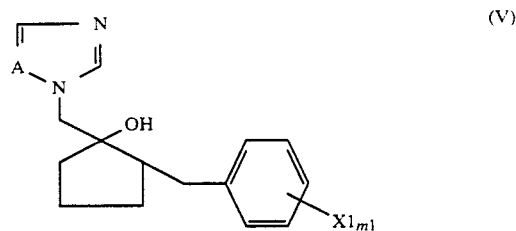

(where
$X_1$ is a halogen atom, an alkyl group, a haloalkyl group, a phenyl group, a cyano group or a nitro group;
A is a nitrogen atom or a CH group; and
$m_1$ is 0 or an integer from 1 to 5 and when $m_1$ is greater than 1 each $X_1$ can be the same or different); and

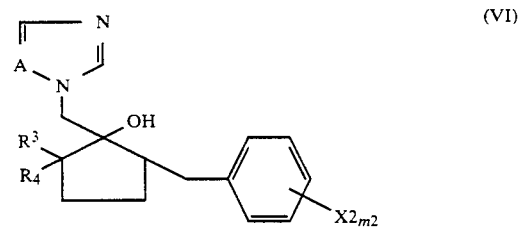

(where
$R_3$ and $R_4$ are identical to or different from each other and each is a hydrogen atom or a lower alkyl group having from 1 to 5 carbon atoms, provided that the case is excluded, where $R_3$ and $R_4$ are each a hydrogen atom at the same time;
$X_2$ is a halogen atom, an alkyl group having from 1 to 5 carbon atoms or a phenyl group;
A is a nitrogen atom or a CH group; and $m_2$ is 0, 1 or 2).

The azole derivative as represented by the general formula (III) to be employed in the reaction as have been described hereinabove may include, for example, a 1,2,4-triazole and an imidazole.

The solvent to be employed for the reaction may include, for example, an amide such as N,N-dimethylformamide, N,N-dimethylacetamide, N-methylpyrrolidone, etc., a nitrile such as acetonitrile, etc., a ketone such as acetone, methyl ethyl ketone, etc., a sulfur-containing compound such as dimethylsulfoxide, sulfolan, etc., an ether such as diethyl ether, tetrahydrofuran, etc., and the like.

The reaction may be carried out at temperatures ranging from approximately −40° C. to 60° C., preferably from approximately −10° C. to 30° C.

The azolylmethylcyclopentanol derivatives as represented by the general formula (IV) can be isolated from the resulting reaction mixture by conventional methods for isolating the objective compound from the reaction mixture, such as column chromatography.

The 1,3,2-dioxathiolan-S-oxide derivative as represented by the general formula (I) (hereinafter also referred to as the "present compound") is used a fungicidal composition, it is generally used in the form of dust, wettable powder, granules, emulsion and the like together with carriers or other adjuvants. In such a case, the preparations are prepared so as to contain one or more of the compound of this invention in an amount of 0.1%-95% by weight, preferably, 0.5%-90% by weight, and more preferably 2%-70% by weight.

The auxiliary agent to be employed for the preparation may include, for example, a carrier, a diluent, a surfactant and the like, which have conventionally been employed as auxiliary agents for the preparation of fungicides.

The carrier in the form of a solid material may include, for example, talc, kaolin, bentonite, diatomaceous earth, white carbon, clay, and the like; the diluent in the form of a liquid may include, for example, water, xylene, toluene, chlorobenzene, cyclohexane, cyclohexanone, dimethylsulfoxide, dimethylformamide, an alcohol, and the like.

The surfactant may preferably be chosen depending upon the forms of the preparations; an emulsifiable agent may include, for example, polyoxyethylene alkyl aryl ether, polyoxyethylene sorbitan monolaurate, and the like; a dispersing agent may include, for example, a lignin sulfonate, a dibutylnaphthalene sulfonate, and the like; and a wetting agent may include, for example, an alkyl sulfonate, an alkylbenzene sulfonate, and the like.

The above preparations are classified into those which can be used directly, and those which are used after diluting so as to have a suitable concentration with a diluent such as water, etc..

The concentration of the present compounds in case of using after diluting is preferred to be in a range of 0.001%-1.0%.

Further, the application dosage of the compound of this invention is in a range of 20 g-5,000 g and preferably 50 g-1,000 g per 1 ha of agricultural and horticultural land such as farm, paddy field; fruit garden, hothouse, etc..

It is of course possible to increase and decrease the concentration and the application dosage beyond the above-mentioned ranges, because they depend upon the form of preparations, method of application, place to be used, target crops, etc..

It is further to be noted that the present compounds may be employed in combination with other active compounds, such as fungicides, insecticides, miticides, herbicides, and the like.

A specific description will now be made of examples of the preparation of the present compounds, examples of uses as intermediate compounds, examples of preparations and examples of tests.

The present invention is not limited to the following examples so far as not coming over the essential features thereof.

The present invention will first be described by way of examples of the preparation of the specific compounds.

PREPARATION EXAMPLE 1:

Synthesis of 9-[(4-chlorophenyl)methyl]-6,6-dimethyl-1,3,2-dioxathiaspiro[4.4]nonan-2-oxide (Compound No. I-I-1)

Into a 200-ml three-necked flask was charged 100 ml of dichloromethane which in turn was stirred under nitrogen streams while cooled with ice. In this solution was dissolved 10.75 grams (0.04 mole) of 5-[(4-chlorophenyl)methyl]-1-hydroxy-2,2-dimethylcyclopentanemethanol ($R_1=CH_3$, $R_2=CH_3$ and $Xm=4$-Cl in the general formula (II) above), and 16.22 grams (0.16 mole) of triethylamine was added to the resulting solution.

Into this solution was dropwise added a solution of 7.16 grams (0.06 mole) of thionyl chloride in 20 ml of dichloromethane. The dropwise addition was implemented by paying attention to the fact that no white fumes would be caused to occur and the reaction was carried out within the range of temperatures between 10° C. and 20° C. The solution was then stirred for 15 minutes while cooling it with ice, followed by adding 100 ml of dichloromethane to the resulting reaction mixture and washing it with 1N-hydrochloric acid and water. The separated organic layer was then dried over anhydrous sodium sulfate and concentrated under reduced pressure, thereby leaving a black oily material in the amount of 15.22 grams.

The oily material was purified through silica gel column chromatography, and the eluate was concentrated to give a crystalline material which in turn was washed with petroleum ether, thereby yielding 9-[(4-chlorophenyl)methyl]-6,6-dimethyl-1,3,2-dioxathiaspiro[4.4-]nonan-2-oxide (Compound No. I-I-1) as white crystal in the quantity of 12.37 grams (39.3 mmole).

The percentage yield and the physical properties of the compound (I-I-1) are as follows:
Yield: 98%
mp: 83° C.-85° C. (a mixture of two isomers)
MS: $M^+=314$ (6%), $M^++2=316$ (2%)

It was found that the compound prepared hereinabove was a mixture of two isomers so that a portion of the compound was purified through silica gel column chromatography into two isomers. The physical properties of the two isomers are measured and they will be indicated as follows:

(a) Isomer A:
mp: 103° C. to 104° C.
$^1$H-NMR (CDCl$_3$) δ 0.97 (s, 6H), 1.17-2.0 (m, 4H), 2.2-3.1 (m, 3H), 4.43 (s, 2H), 7.2 (m, 4H)
IR (KBr, $\nu_{max}$): 2968, 2876, 1498, 1202 (S=0), 1092, 950, 928, 850, 838, 786 cm$^{-1}$ (b) Isomer B:
mp: 118° C. to 119° C.
$^1$H-NMR (CDCl$_3$): δ 0.93 (s, 3H), 1.1 (s, 3H), 1.23-1.93 (m, 4H), 2.07-3.0 (m, 3H), 4.23 (d, 1H, J=8Hz), 4.5 (d, 1H, J=8Hz), 7.03 (d, 2H, J=8Hz), 7.2 (d, 2H, J=8Hz)
IR (KBr, $\nu_{max}$): 2976, 2876, 1496, 1202 (S=0), 1092, 952, 926, 842, 820, 794 cm$^{-1}$

PREPARATION EXAMPLE 2:

Synthesis of 9-[(4-chlorophenyl)methyl]-6,6-dimethyl-1,3,2-dioxathia-spiro[4.4]nonane-2,2-dioxide (Compound No. I-II-1)

Into a 300-ml Erlenmeyer flask was charged 4.38 grams (14 mmole) of the compound (I-I-1) prepared in Example 1 above (as the mixture of the two isomers), and 50 ml of carbon tetrachloride, 50 ml of acetonitrile, and 75 ml of water were added to the compound. After stirring the mixture while cooling with ice, 14.5 mg (0.07 mmole; 0.5 mole %) of RuCl$_3$ and 6.02 grams (28 mmole; 2 mole-eq.) of NaIO$_4$ were added to the mixture, and the resulting mixture was stirred while cooling it with ice.

After 1 hour, the reaction mixture was mixed with 100 ml of ether, thereby separating it into the aqueous layer and the organic layer. The aqueous layer was extracted with ether, and the extract was combined with the organic layer, followed by drying it over anhydrous sodium sulfate and concentrating it under reduced pressure, thereby yielding a pale yellow oily material in the amount of 4.47 grams.

The oily material was then purified with silica gel column chromatography, leaving 9-[(4-chlorophenyl)-methyl]-6,6-dimethyl-1,3,2-dioxathiaspiro[4.4]nonane-2,2-dioxide (Compound No. I-II-1) as a white crystalline compound in the amount of 4.38 grams (13.5 mmole).

The percentage yield and the physical properties of the compound (I-II-1) are as follows:

Yield: 96.4%
mp: 98° C.–100° C.

$^1$H-NMR (CDCl$_3$): δ 0.97 (s, 3H), 1.2 (s, 3H), 1.33–2.0 (m, 4H), 2.1–2.6 (m, 1H), 2.6–3.27 (m, 2H), 4.43 (d, 1H, J=9Hz), 4.6 (d, 1H, J=9Hz), 7.07 (d, 2H, J=8Hz), 7.27 (d, 2H, J=8Hz)

IR (KBr, $\nu_{max}$) 2980, 2870, 1498, 1478, 1374 (S=O), 1206 (S=O), 964, 872, 850 cm$^{-1}$

PREPARATION EXAMPLE 3:

Synthesis of 9-[(4-chlorophenyl)methyl]-6,6-dimethyl-1,3,2-dioxathia-spiro[4.4]nonane-2,2-dioxide (Compound No. I-II-1)

Into a 100-ml Erlenmeyer flask was charged 1.14 grams (3.62 mmole) of the compound (I-I-1) prepared in Example 1 above (as the mixture of the two isomers), and 20 ml of acetonitrile and 30 ml of water were added to the compound. After stirring the mixture while cooling with ice, 4.0 mg (0.019 mmole; 0.52 mole %) of RuCl$_3$ and 1.55 grams (7.24 mmole; 2 mole-eq.) of NaIO$_4$ were added to the mixture, followed by stirring it under cooling with ice. The starting material disappeared in 0.5 hour.

To the reaction mixture was added 100 ml of ether, and the reaction mixture was separated into the aqueous layer and the organic layer. The aqueous layer was extracted with ether, and the extract was combined with the organic layer, followed by drying it over anhydrous sodium sulfate, filtering out the sodium sulfate, and concentrating it under reduced pressure, thereby yielding a pale yellow solid material.

The solid material was then washed with ether, leaving 9-[(4-chlorophenyl)methyl]-6,6-dimethyl-1,3,2-dioxathiaspiro[4.4]nonane-2,2-dioxide (Compound No. I-II-1) as a white crystalline compound in the amount of 1.13 grams (3.42 mmole).

The percentage yield and the physical properties of the compound (I-II-1) are as follows:

Yield: 94.5%
mp: 98° C.–100° C.

$^1$H-NMR (CDCl$_3$): δ 0.97 (s, 3H), 1.2 (s, 3H), 1.33–2.0 (m, 4H), 2.1–2.6 (m, 1H), 2.6–3.27 (m, 2H), 4.43 (d, 1H, J=9Hz), 4.6 (d, 1H, J=9Hz), 7.07 (d, 2H, J=8Hz), 7.27 (d, 2H, J=8Hz)

IR (KBr, $\nu_{max}$): 2980, 2870, 1498, 1478, 1374 (S=O), 1206 (S=O), 964, 872, 850 cm$^{-1}$

PREPARATION EXAMPLE 4:

Preparation of cis-5-[(4-chlorophenyl)methyl]-2,2-dimethyl-1-(1H-1,2,4-triazol-1-ylmethyl)cyclopentanol (IV-1)

Oily sodium hydride (60%; 24.3 mg; 0.6 mmole) was washed with n-hexane, and 3 ml of dimethylformamide (DMF) was added, followed by stirring the mixture at room temperature. To the resulting mixture was added 41.4 mg (0.6 mmole) of 1,2,4-triazole, and the mixture was stirred for 10 minutes, followed by dropwise addition of 1 ml of a DMF solution of 0.1654 gram (0.5 mmole) of the compound (I-II-1) to the resulting mixture.

The mixture was then stirred at room temperature for 3 hours and the reaction mixture was treated in conventional manner, thereby leaving a red oil material in the amount of 0.2026 gram.

The oily material was then dissolved in 3 ml of tetrahydrofuran (THF), and 0.1 ml of concentrated sulfuric acid and 0.1 ml of water were added to the solution. After the solution was stirred at room temperature for 1 hour, it was neutralized with 1 gram of potassium carbonate and 3 ml of water and then treated in conventional manner, thereby leaving a yellow oily material in the amount of 0.1357 gram.

The yellow oil material was then purified through column chromatography with silica gel (Wakogel C-300 ®; 10 grams) by using a hexane:ethyl acetate (5:1) mixture as a developing solution, thereby yielding the compound (IV-1) as a white crystalline substance in the amount of 70.4 mg (0.22 mmole).

The percentage yield and the physical properties of the compound (IV-1) are as follows:

Yield: 44%
mp: 113° C.–114° C.

$^1$H-NMR (CDCl$_3$): δ 0.60 (s, 3H), 1.00 (s, 3H), 1.07–1.19 (m, 5H), 2.33 (bs, 2H), 3.53 (bs, 1H), 4.13 (s, 2Hz), 7.06 (d, 2H, J TM 8Hz), 7.25 (d, 2H, J=8Hz), 8.02 (s, 1H), 8.25 (s, 1H)

IR (KBr, $\nu_{max}$): 3250, 2940, 2850, 1480, 1380, 1262, 1200, 1124, 1080, 1002, 840, 800, 720, 670 cm$^{-1}$

FORMULATION EXAMPLES

The following examples are directed to the formulations or preparations containing the 1,3,2-dioxathiolan-S-oxide derivative as represented by the general formula (I) as an active ingredient.

| Formulation Example 1: Dust | |
|---|---|
| 9-[(4-chlorophenyl)methyl]-6,6-dimethyl-1,3,2-dioxathia-spiro[4.4]nonan-2-oxide (Compound No. I-I-1) | 3 parts by weight |
| Clay | 40 parts by weight |
| Talc | 57 parts by weight |

The above-mentioned ingredients were mixed to prepare a dust.

| Formulation Example 2: Wettable Powder | |
|---|---|
| 9-[(4-chlorophenyl)methyl]-6,6-dimethyl-1,3,2-dioxathia-spiro[4.4]nonane-2,2-dioxide (Compound No. I-II-1) | 50 parts by weight |
| Lignin sulfonate | 5 parts by weight |
| Alkyl sulfonate | 3 parts by weight |
| Diatomaceous earth | 42 parts by weight |

The above-mentioned ingredients were mixed to prepare a wettable powder. This preparation was used in situ by diluting it with water.

| Formulation Example 3: Granules | |
|---|---|
| Compound (I-I-1) | 5 parts by weight |
| Bentonite | 43 parts by weight |
| Clay | 45 parts by weight |

-continued

| Formulation Example 3: Granules | |
|---|---|
| Lignin sulfonate | 7 parts by weight |

The above-mentioned ingredients were mixed and kneaded with adding water thereto. The mixture was granulated by means of an extrusion granulating machine, followed by drying to obtain granules.

| Formulation Example 4: Emulsion | |
|---|---|
| Compound (I-II-1) | 20 parts by weight |
| Polyoxyethylene alkyl aryl ether | 10 parts by weight |
| Polyoxyethylene sorbitan monolaurate | 3 parts by weight |
| Xylene | 67 parts by weight |

The above-mentioned ingredients were mixed and dissolved to obtain an emulsion.

ANTIBACTERIAL TESTS

The 1,3,2-dioxathiolan-S-oxide derivatives (I-I-1) and (I-II-1) were tested for antifungal activities against various plant pathogenic fungi.

TEST PROCEDURES

Each of the 1,3,2-dioxathiolan-S-oxide derivatives (I-I-1) and (I-II-1) was dissolved in dimethylsulfoxide in a suitable concentration, 0.6 ml of the solution was well mixed with 60 ml of a PAS culture medium at about 60° C. in a 100 ml conical flask, and the resultant mixture was poured into petri dishes and was caused to coagulate, by which plate culture media containing the compound of this invention were obtained.

On the other hand, plate culture media on which test fungi were previously cultured were punched by a cork borer so as to have a diameter of 4 mm, followed by inoculating on the above-mentioned plate culture medium. After inoculation was carried out, they were incubated for 1-3 days at a preferable temperature for each fungus and growth of fungi was observed by measuring the diameter of the colony. Hyphae elongation inhibitory rates were determined respectively in accordance with the below described equation:

$$R = 100(dc - dt)/dc$$

where
R = Hyphae elongation inhibitory rate (%)
dc = Diameter of colony on the non-treated plate culture medium
dt = Diameter of colony on the plate culture medium containing the tested compound The results were ranked in three stages by the following ranking system.
0: R is lower than 50%;
1: R is between 50% and 80%; and
2: R is higher than 80%.

The results against the test fungi will be shown in Table 2 below.

TABLE 2

| Compound Nos. | Concentration (μg/ml) | Test Fungi | | | | |
|---|---|---|---|---|---|---|
| | | H.s | R.s. | C.l. | S.c. | G.c. |
| I-I-1 | 100 | 2 | 2 | 1 | 2 | 1 |
| I-II-1 | 100 | 2 | 2 | 2 | 2 | 2 |

The abbreviations for the test fungi in Table 2 above are as follows:
H.s.: *Helminthosporium sigmoideum*
R.s.: *Rhizoctonia solani*
C.l.: *Colletotrichum langenarium*
S.c.: *Sclerotinia sclerotirum*
G.c.: *Glomerella cingulata*

What is claimed is:

1. A 1,3,2-dioxathiolan-S-oxide derivative as represented by the general formula (I):

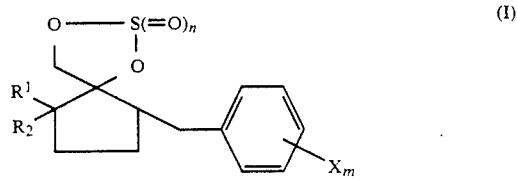

where
$R_1$ and $R_2$ are identical to or different from each other and each is a hydrogen atom or a lower alkyl group;
X is a halogen atom, a cyano group, a lower alkyl group, a haloalkyl group or a phenyl group;
m is 0 or an integer from 1 to 5 and when m is greater than 1 each X can be the same or different; and n is 1 or 2.

2. A 1,3,2-dioxathiolan-S-oxide derivative as claimed in claim 1, wherein $R_1$ is methyl, $R_2$ is methyl, $X_m$ is chlorine atom, and n is 1 or 2.

3. A 1,3,2-dioxathiolan-S-oxide derivative as claimed in claim 2, wherein the chlorine atom in $X_m$ is positioned in the para-position of the phenyl group.

4. A fungicidal composition containing, as an active ingredient, a 1,3,2-dioxathiolan-S-oxide derivative as represented by the general formula (I):

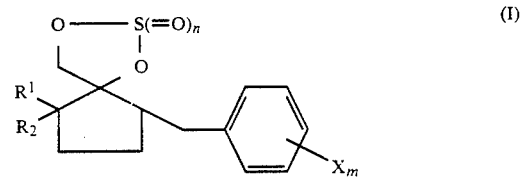

where
$R_1$ and $R_2$ are identical to or different from each other and each is a hydrogen atom or a lower alkyl group;
X is a halogen atom, a cyano group, a lower alkyl group, a haloalkyl group or a phenyl group;
m is 0 or an integer from 1 to 5 and when m is greater than 1 each X can be the same or different; and n is 1 or 2 and an inert carrier therefor.

5. A composition as claimed in claim 4, wherein $R_1$ is methyl, $R_2$ is methyl, $X_m$ is chlorine atom, and n is 1 or 2.

* * * * *